United States Patent [19]
Davenport et al.

[11] Patent Number: 5,841,800
[45] Date of Patent: Nov. 24, 1998

[54] DESKTOP MEDICAL LASER GENERATOR

[75] Inventors: Scott A. Davenport, Half Moon Bay; Michael Hodel, Fremont, both of Calif.

[73] Assignee: Laserscope, San Jose, Calif.

[21] Appl. No.: 508,517

[22] Filed: Jul. 28, 1995

[51] Int. Cl.[6] ........................................... H01S 3/10
[52] U.S. Cl. .............................................. 372/22
[58] Field of Search ............................. 372/22; 359/326

[56] References Cited

U.S. PATENT DOCUMENTS

| | | | |
|---|---|---|---|
| 4,907,235 | 3/1990 | Kuizenga | 371/21 |
| 5,025,446 | 6/1991 | Kuizenga | 372/21 |
| 5,243,615 | 9/1993 | Ortiz et al. | 372/22 |
| 5,345,457 | 9/1994 | Zenzie et al. | 372/22 |

*Primary Examiner*—Rodney B. Bovernick
*Assistant Examiner*—Robert E. Wise
*Attorney, Agent, or Firm*—Innovation Law Group

[57] ABSTRACT

A desktop medical laser generator (10) for laser surgery has a base plate (12) and an optical assembly (14) mounted thereon. The optical assembly (14) has an improved lamp housing (16) having two identical shell sections (44) and associated components for housing a YAG rod (60) and a lamp (58). Light emitted from the lamp housing (16) is doubled in frequency by a KTP crystal (26), monitored by two power detectors (32,34) and emitted through an output connector (36). A line power control system (90) insures the current drawn from a standard wall receptacle (80) does not exceed accepted limits. An output power detection system (90) closely monitors output power.

5 Claims, 4 Drawing Sheets

DESKTOP MEDICAL LASER GENERATOR

TECHNICAL FIELD

The present invention relates to the field of laser surgery and therapy, and more particularly to an improved laser light generation and control device. The predominant current usage of the present inventive laser generator is in precision surgery and therapy wherein it is desirable to produce laser light of different wavelengths at controlled energy levels.

BACKGROUND ART

Lasers are widely used in the medical field in surgical and therapeutic applications. It is known in the art to provide laser energy for such applications at different frequencies tailored to specific applications. It is further accepted in the field that it is extremely desirable to provide a variable power output such that the practitioner can carefully control the rate of energy delivery to a treatment site. A frequency doubled laser using a KTP frequency doubling crystal is taught by U.S. Pat. No. 5,249,192 issued to Kuizenga et al., and the green light produced by such a laser has proven to be particularly valuable for many medical applications. It is also known in the art to provide a "Z" optical configuration, as is illustrated in the disclosure of U.S. Pat. No. 5,130,997, issued to Ortiz et al., as a practical means for incorporating a non-linear optical component (such as a KTP crystal) into a reasonably sized laser generating apparatus.

All of the above improvements and innovations found in the prior art have proven to be valuable additions to the medical field. However, the incorporation of these improvements, and others not specifically mentioned, into a unit which can be used for laser surgery and therapy has resulted in apparatus which is both bulky and expensive, and which cannot be used without special power connections, and the like. It would be advantageous to have a smaller and less expensive unit which could be plugged directly into a readily available 110/115 volt power outlet for operation. However, prior to the present invention, the problems associated with making such a unit have seemed insurmountable. Among the problems associated with making a medical laser such that it is smaller and have been that atenuators have been necessary to allow a variable power output, and a relatively large size has been necessary to allow for sufficient heat dissipation. Among the problems associated with making a unit which can be powered from a standard wall outlet are that insufficient power has been available therefrom, using prior art means, to deliver the amount of power required at the laser output. Among the problems associated with making a unit which is relatively inexpensive are the substantial costs associated with the lamp housing of prior art units and the previously mentioned attenuators (which both take additional space and add to the cost of prior art units).

DISCLOSURE OF INVENTION

Accordingly, it is an object of the present invention to provide an improved laser generation device which will deliver accurately controlled amounts of laser energy.

It is still another object of the present invention to provide an improved laser generation device which is sufficiently small to be portable.

It is yet another object of the present invention to provide an improved laser generation device which avoids the expense, complication and other problems associated with attenuation means.

It is still another object of the present invention to provide a medical laser generation device which is small, light in weight, and convenient to operate in comparison to conventional medical laser generation devices.

It is yet another object of the present invention to provide a medical laser generation device which inherently is inexpensive to manufacture and to maintain.

It is still another object of the present invention to provide a medical laser generation device which can be powered from a standard wall outlet while still delivering sufficient laser power.

Briefly, the preferred embodiment of the present invention is a laser generation device incorporating, in operative combination, a unique optical design whereby the laser can be operated stably at low power levels, such that no attenuation is required when less than maximum power is required at the output. A unique lamp housing, having "mirror image" construction adds to the stability, decreased size and increased reliability of the unit, while greatly reducing overall cost. Since the laser must, in order to meet necessary output power levels, operate at near the maximum allowable current draw from a 110 volt power source, the input current is monitored and the power gain of the laser unit is adjusted accordingly. An improved output power monitoring means is employed to more accurately measure and control the output power from the desktop medical laser generator.

An advantage of the present invention is that it is smaller an comparable prior art units.

A further advantage of the present invention is that the laser generator is inherently stable.

Yet another advantage of the present invention is that no special wiring or electrical power outlet is required.

Still another advantage of the present invention is that the inventive desktop medical laser generator is inherently less expensive to produce than comparable prior art units.

Yet another advantage of the present invention is that it is inexpensive to maintain.

Still another advantage of the present invention is that output power can be more accurately monitored and controlled.

These and other objects and advantages of the present invention will become clear to those skilled in the art in view of the description of the best presently known mode of carrying out the invention and the industrial applicability of the preferred embodiment as described herein and as illustrated in the several figures of the drawing.

BEST MODE FOR CARRYING OUT THE INVENTION

Figure 1:
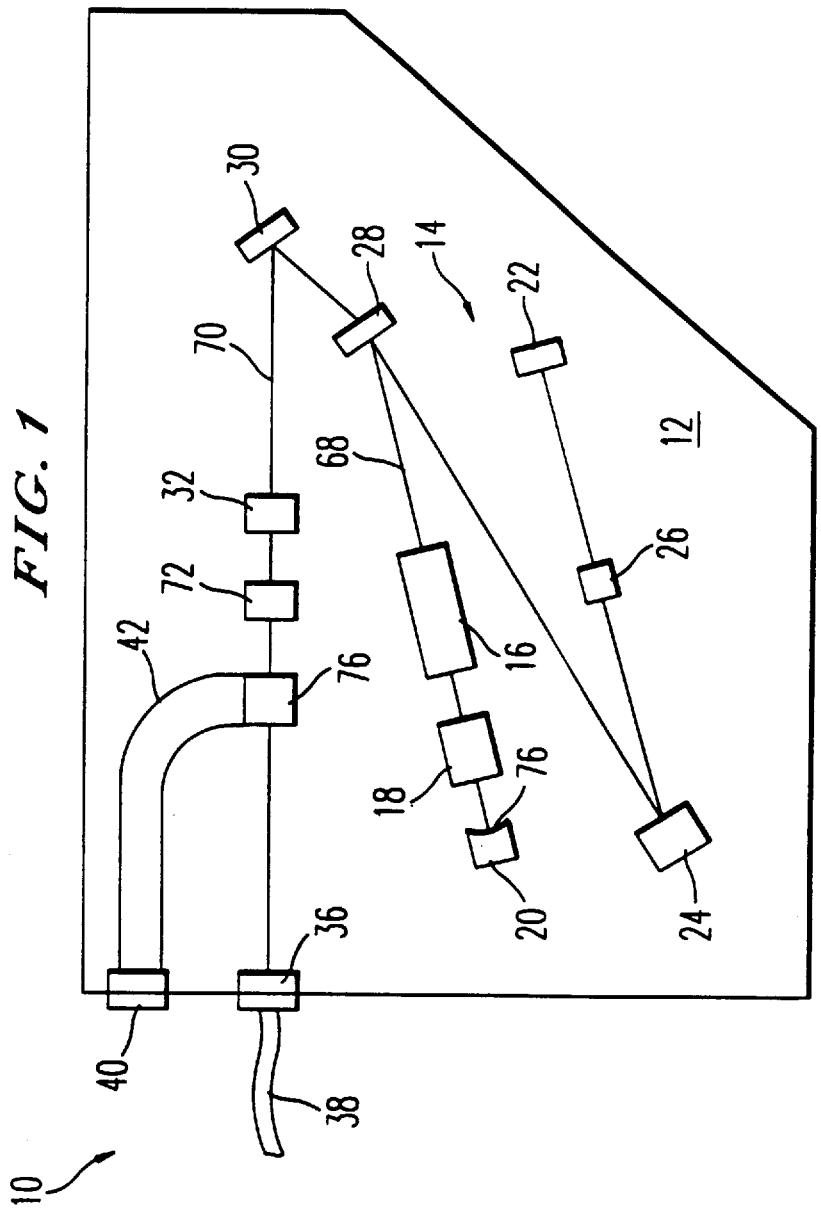
FIG. 1 is a diagrammatic plan view of a desktop medical laser generator according to the present invention.

The following detailed description illustrates the invention by way of example, not by way of limitation of the principles of the invention. The best presently known mode for carrying out the invention is a desktop medical laser generator for delivering laser light at controlled power levels and for controlled times. The predominant current usage of the desktop medical laser generator is for use with a laser delivery device, such as a laser surgical handpiece (sometimes called a "laser scalpel") to perform surgery using the laser light as a cutting means. The inventive desktop medical laser generator is depicted in a diagrammatic plan view in the view of FIG. 1, and is designated therein by the general reference character 10.

The desktop medical laser generator 10 has a base plate 12 with an optical assembly 14 mounted thereon. The optical assembly 14 has a lamp housing 16, a Q switch 18, a LAM mirror 20, a SAM mirror 22 and a RAM mirror 24. (Note that the names, "SAM", "LAM" and "RAM", and such, as used herein—are historical in nature. For example, LAM is derived from "long arm" and SAM from "short arm". These terms had significance when some prior art laser optical arrangements were generally "L" shaped—with a long arm and a short arm. As used herein, these terms are not particularly associated with their historical meanings. Rather, they are just terms used to designate the different specific components associated with each of the terms.)

The optical assembly 14 further has a KTP crystal 26, an output coupler 28, a turning mirror 30, a surgical detector 32 and a safety detector. An output connector 36 couples the light output of the desktop medical laser generator 10 to an optical cable 38, the distal end of which (not shown) will be connected to a laser handpiece (not shown) or other means for delivering the laser light energy produced by the desktop medical laser generator 10 a surgical site. A calibration port 40 provides a means for returning light from the optical cable 38 to the safety detector 34 through a light pipe 42. The calibration port 40 and the light pipe 42 comprise a part of a calibration means which is the subject of a copending patent application of Coleman et al., filed Jul. 28, 1995, entitled "IMPROVED FIBER OPTICS CALIBRATION DEVICE".

Figure 2:
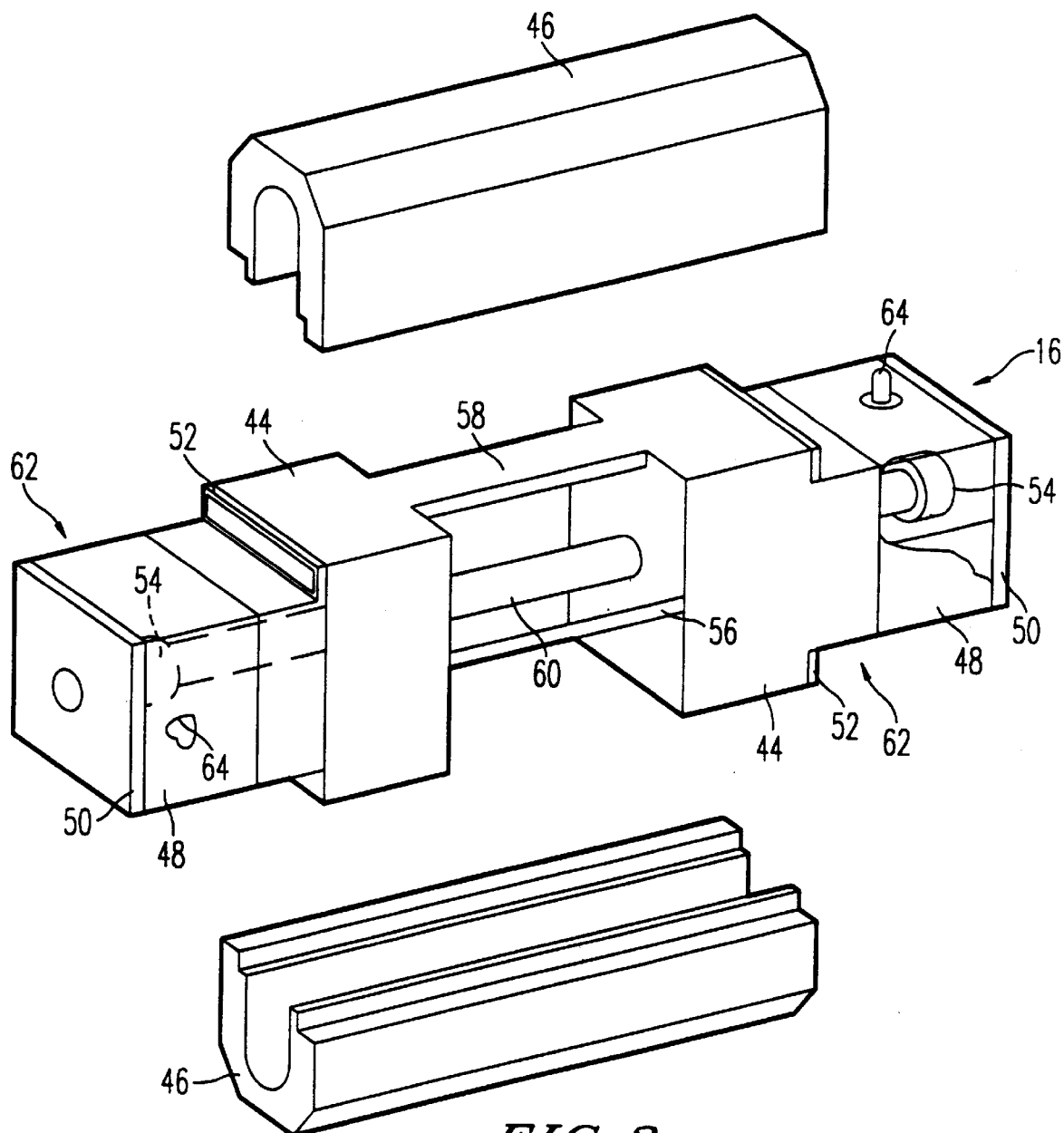
FIG. 2 is an exploded perspective view of a lamp housing according to the present invention.
Figure 3:
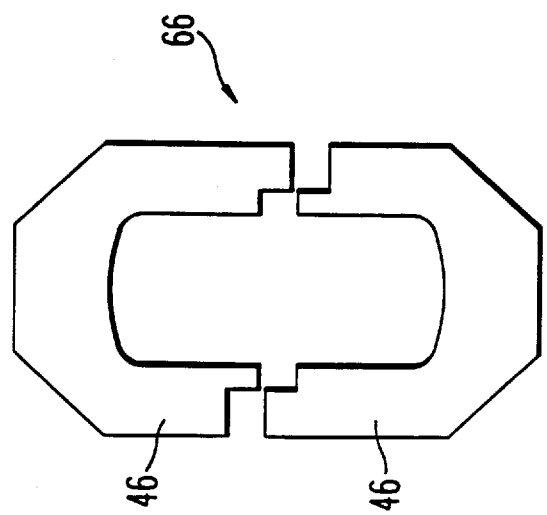
FIG. 3 is an elevational end view of the ceramic reflector unit of FIG. 2.

FIG. 2 is an expanded perspective view of the lamp housing 16 of FIG. 1. The lamp housing 16 has two shell sections 44, two ceramic reflectors 46, two insulators 48, two covers 50, two seal plates 52, two terminals 54 and a slide 56. Within the lamp housing 16 is an elongated lamp 58 and, running generally parallel thereto, a YAG rod 60. As can be appreciated from the view of FIG. 2, one each of a shell section 44, a ceramic reflector 46, an insulator 48, a cover 50, a seal plates 52, and a terminal 54 are assembled into a lamp housing half 62, with two identical lamp housing halves being interconnected to form the lamp housing 16. Cooling of the lamp housing 16 is enhanced by substantial contact with the relatively massive base plate 12, and further by water cooling circulated through a plurality of water ports 64. It should be noted that according to the present invention, the present inventive lamp housing 16 is not only substantially smaller than was previously thought possible, but is also substantially less expensive to manufacture due in primary part to the fact that the lamp housing halves 62 (and components thereof are identical, and so there is considerable savings in tooling costs. FIG. 3 is a end view of the two ceramic reflectors 46 showing how the two ceramic reflectors 46 fit together to form a ceramic reflector unit 66.

Referring again to FIG. 1, the Q switch 18 is a known device wherein silica is bonded onto a piezo electric transducer. When RF power (at 27 MHz, in the present application) is applied to the piezo electric transducer an acoustic wave is produced in the silica that propagates into a diffraction grating, thus preventing passage of light therethrough. In the best presently known embodiment 10 of the present invention, the positioning of the Q switch 18 between the lamp housing 16 and the LAM mirror 20 prevents lasing in the YAG rod 60 in housing 16 (see FIG. 2) when the Q switch 18 is activated, thereby allowing a high population inversion build up to a saturation level in the YAG rod. In the best presently known embodiment 10 of the present invention, the Q switch 18 is switched to allow lasing approximately at 40 micro second intervals. When the Q switch is turned off the YAG rod 60 will lase at a power controlled generally by the power applied to the lamp 58 (see FIG. 2).

The LAM mirror 20 and the SAM mirror 22 and the RAM mirror 24 are highly reflective mirrors, and the output coupler 28 is highly reflective to infrared, while allowing green light to pass. An infrared laser light beam 68 emitted from the lamp housing 16 will circulate within the optical assembly 14 reflecting from the LAM mirror 20, the output coupler 28, the RAM mirror 24 and the SAM mirror 22 and passing through the KTP crystal 26, as depicted in the view of FIG. 1. As the infrared laser light beam 68 passes through the KTP crystal 26 it will tend to become doubled in frequency and will become a green laser light beam 70. The green laser light beam 70 will travel the same path within the optical assembly 14 described previously herein in relation to the infrared laser light beam 68, except that when the green laser light beam strikes the output coupler 28 it will pass therethrough and then reflect from the turning mirror 30, through the surgical detector 32, through a safety shutter assembly 72, through the safety detector 34 and out of the output connector 36. The surgical detector 32 is used to detect the output power of the desktop medical laser 10. The safety detector 34 serves as a secondary detector to detect overpower conditions such as might result from a malfunction of the surgical detector 32 or other power control circuitry, or the like.

During normal operation of the desktop medical laser 10, when the safety detector 34 detects an unsafe output power condition then the safety shutter assembly 72 will shut preventing passage of the green laser light beam 70 therethrough. As previously mentioned, herein, the best presently known embodiment 10 of the present invention includes a calibration apparatus 74 which is the subject of the aforementioned copending patent application. For purposes of the present disclosure it should be noted that the safety detector 34 performs a different function than that described herein in when being used in conjunction with the calibration apparatus 74.

In order to increase the efficiency of the desktop medical laser generator 10 and to increase stability at lower power levels such that attenuators are not needed to provide lowered power output at the output connection, a reflective surface 76 of the LAM mirror 20 of the best presently known embodiment 10 of the present invention is concave (as compared to the flat mirrors of the prior art), such that the reflective surface has a radius of 100 cm. Also, the magnification ratio of the optical assembly 14 (the ratio of the focal length of the output coupler 28 divided by the focal length of the RAM mirror 24) of the desktop medical laser generator 10 is approximately 3.3— as compared to a typical ratio of 2.5 in the prior art, although changes in this general range would have essentially the same general effect.

Figure 4:
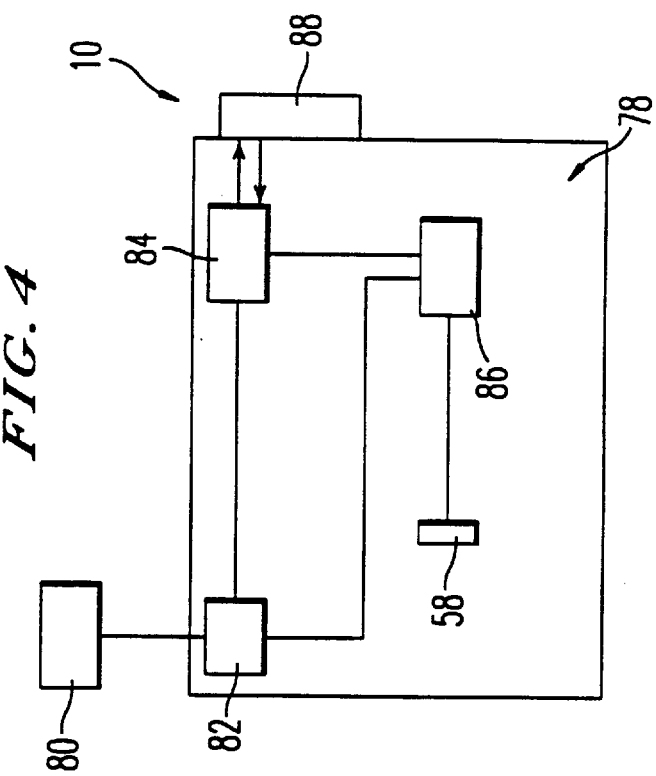
FIG. 4 is a block schematic of a line current monitor and control apparatus according to the present invention.

FIG. 4 is a diagrammatic depiction of a portion of the desktop medical laser 10 depicting specifically a line power control system 78 according to the present invention. In order to allow the desktop medical laser 10 to operate from a standard 110/115 volt wall receptacle 80 a current monitor 82 monitors the current being drawn from the wall receptacle 80. Data advising the instant current level is provided to a microprocessor 84. (It should be noted that the microprocessor 84 performs essentially all of the control and interface functions in the desktop medical laser, including those previously described herein.) When the current monitor 82 advises the microprocessor 84 that the current being drawn from the wall receptacle is too great, then the microprocessor 84 adjusts current being provided to a lamp power supply 86 downward, accordingly. The lamp power supply 86 provides the power, at a constant voltage, to the lamp 58 (see FIG. 2), which draws most of the current used by the desktop medical laser 10. When and if the microprocessor 84 is forced to lower the power provided from the lamp power supply 86 so much that the amount of output power to be provided at the output connector 36 (FIG. 1) cannot be that which the user has requested, then the user is so advised by means of a user interface 88.

Figure 5:
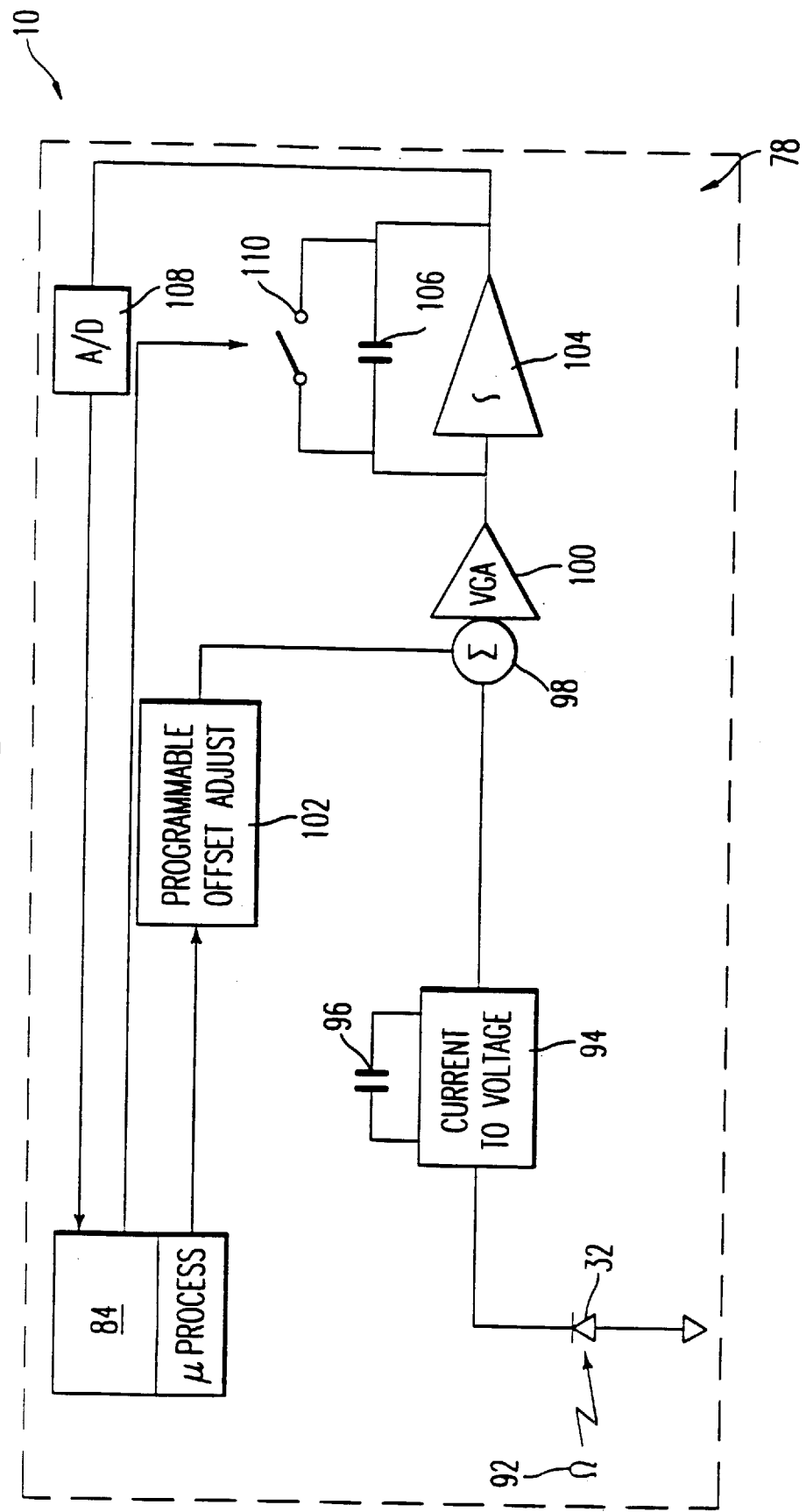
FIG. 5 is a block schematic of an output power detection apparatus according to the present invention.

FIG. 5 is a block schematic diagram of a portion of the desktop medical laser 10 depicting specifically an output power detection system 78 according to the present invention. When a Q switch pulse 92 is produced by the desktop medical laser 10 it is detected by the surgical detector 32. (The Q switch pulse 92 is a single light pulse produced at the output connector (FIG. 1) each time the Q switch 18 is pulsed to allow the YAG rod 60 to lase. In the best presently known embodiment 10 of the present invention, the Q switch pulse 92 will be about 2 micro seconds in duration). The current output of the surgical detector 32 is converted to an equivalent voltage output by a current to voltage convertor 94. The current to voltage convertor 94 has a band width determined by a selectable band limiting capacitor 96. (In the best presently known embodiment 10 of the present invention, the band limiting capacitor 96 is selected such that the band width of the current to voltage convertor 94 is 100 kHz. to 1 MHz.) Output from the current to voltage convertor 94 is provided to a summing node 98 of avariable gain amplifier 100. Also provided to the summing node 98 is the output of a programmable offset adjust 102. The programmable offset adjust 102 provides a voltage to the summing node 98 to offset a value determined by the microprocessor 84 to compensate for output from the surgical detector 32 when no Q switch pulse 92 is present (that is, when there is no output from the desktop medical laser 10). In the best presently known embodiment 10 of the present invention, the variable gain amplifier 100 will be set at a 1× for a bandwidth of 2.8 MHz, at 5× for a bandwidth of 1.6 MHz and at 20× for a bandwidth of 1 MHz. Output of the variable gain amplifier 100 is provided to an integrating amplifier 104 which has an integrating capacitor 106 configured such that pulses output from the variable gain amplifier 100 are accumulated in the integrating capacitor 106 with the accumulated voltage available at the output of the integrating amplifier 104. The output of the integrating amplifier 104 is converted to by an analog to digital convertor 108 and periodically, (about every 100 milliseconds, in the best presently known embodiment of the invention) the output of the integrating amplifier is read by the microprocessor 84, whereafter the microprocessor 84 momentarily closes a reset switch 110, discharging the integrating capacitor 106, and the process is resumed as described above. This detection process operates the same for the safety detector 34 as has just been described in relation to the surgical detector 32.

Various modifications may be made to the invention without altering its value or scope. For example, the frequencies, bandwidths, and periods as described herein in relation to the best presently known embodiment 10 of the present invention are subject to modification so long as the basic parameters of the invention as described herein are maintained.

INDUSTRIAL APPLICABILITY

The inventive desktop medical laser generator 10 is intended to be widely used for any surgical procedure that needs cutting and simultaneous coagulation, and for many other laser surgery applications wherein it might be desirable to be able vary the energy density of a laser beam. As has been previously discussed herein, the desktop medical laser generator 10 is easily transported such that special economy is derived from the fact that, in many instances, it is anticipated that a medical facility might require fewer of the desktop medical laser generators 10 (as compared to the quantity of larger prior art units required). Since the present inventive desktop medical laser generator 10 can be plugged into existing wall power outlets, no special connections or arrangements (other than the water or vacuum found in essentially every operating room) are required. In operation, the present inventive desktop medical laser generator 10 will not differ substantially from those prior art units which are capable of producing laser light in the same spectral range. It is anticipated that existing attachments arid any which might be developed in the future will be attached to and used with the present inventive desktop medical laser generator 10.

Since desktop medical laser generator 10 of the present invention may be readily produced and since it offers the substantial inherent advantages as described herein, it is expected that it will be readily accepted in the industry. For these and other reasons, it is expected that the utility and industrial applicability of the invention will be both significant in scope and long-lasting in duration.

All of the above are only some of the examples of available embodiments of the present invention. Those skilled in the art will readily observe that numerous other modifications and alterations may be made without departing from the spirit and scope of the invention. Accordingly, the above disclosure is not intended as limiting and the appended claims are to be interpreted as encompassing the entire scope of the invention.

We claim:

1. In a medical laser generating apparatus of the frequency doubling type having: a base plate; a lamp housing mounted on said base plate; a lamp and a rod generally enclosed within said lamp housing such that said rod will lase when excited by said lamp, to emit a laser beam from said lamp housing; a first mirror, an output coupling type second mirror, a third mirror and optionally a fourth mirror arranged such that light emitted from said lamp housing will reflect from said first mirror, through said rod, to said second mirror, to said third mirror and optionally to said fourth mirror and back to said third mirror, thence to said second mirror, through said rod and to said first mirror; and a frequency doubling means in the path of said laser beam so that at least one of said first mirror, said second mirror, said third mirror or/and said optional fourth mirror is adapted to reflect light at the frequency produced by the rod and said second mirror pass light at double the frequency produced by the rod the improvement comprising:

a) said first mirror is concave,
b) the ratio of the focal length of said second mirror divided by the focal length of the third mirror is greater than 2.5; and c) the spacing of:
  i) the concave first mirror;
  ii) the frequency doubling means; and
  iii) said second, third and optional fourth mirrors in the system are adjusted with respect to the rod and amongst themselves to provide increased stability at low power levels and without need for attenuators.

2. The medical laser generating apparatus of claim 1, wherein:
the ratio of the focal length of the second mirror divided by the focal length of the third mirror is at least 3.0.

3. The medical laser generator apparatus as in claim 2 wherein the focal length of the first mirror is at least about 100 cm.

4. The medical laser generating device of claim 1, wherein:
the laser generating rod is a YAG rod.

5. The medical laser generator apparatus as in claim 1 wherein the focal length of the first mirror is at least about 100 cm.

* * * * *